United States Patent [19]
Gold et al.

[11] Patent Number: 5,368,058
[45] Date of Patent: Nov. 29, 1994

[54] SAMPLE PORT VALVE

[75] Inventors: Michael K. Gold, Prior Lake; Mathew J. Gold, Hutchinson, both of Minn.

[73] Assignee: Goldeneye Solutions, Inc., Prior Lake, Minn.

[21] Appl. No.: 173,666

[22] Filed: Dec. 23, 1993

[51] Int. Cl.⁵ .............................................. E03B 11/00
[52] U.S. Cl. ........................................ 137/1; 137/315; 137/577; 137/590; 251/297; 251/148
[58] Field of Search .................... 137/1, 315, 577, 590, 137/592; 251/297, 144, 148, 142

[56] References Cited

U.S. PATENT DOCUMENTS

| | | | |
|---|---|---|---|
| 3,510,102 | 5/1970 | Sungaila | 137/577 |
| 3,718,544 | 2/1973 | Sims | 137/577 |
| 4,216,792 | 8/1980 | Siminovich | 137/577 |
| 4,432,760 | 2/1984 | Mittleman et al. | 251/297 |
| 5,131,497 | 7/1992 | Rogers | 137/590 |

OTHER PUBLICATIONS

Bukey, Michael and Byrne, Wes, "Information Exchange", *Ultrapure Water*, Mar./Apr. 1986, pp. 58–62.

*Primary Examiner*—A. Michael Chambers
*Attorney, Agent, or Firm*—Fredrikson & Byron

[57] ABSTRACT

A sample port valve for use in a port of a liquid-containing vessel. The valve incorporates a housing that is attachable to a port of the vessel, such as the permeate port of a reverse osmosis pressure vessel. A preferred valve allows a user to insert and retain a sampling tube into the valve to a position less than fully inserted. With the tube in its inserted, retained position the valve can then be fully opened to allow the tube to be fully inserted into the vessel, without the loss of liquid or pressure from the vessel.

11 Claims, 6 Drawing Sheets

SAMPLE PORT VALVE

TECHNICAL FIELD

The present invention relates to the field of valves and other apparatuses useful for accessing and sampling the liquid contents of containers and vessels. In a preferred aspect, the invention relates to the sampling of the contents of containers such as those used for water purification, including for such processes as reverse osmosis and ultrafiltration. In such a preferred aspect the invention relates to methods and apparatuses for accessing and sampling the permeate stream of reverse osmosis systems, e.g., in order to obtain permeate sample profiles.

BACKGROUND ART

Osmosis is a natural phenomenon that occurs when water from a less concentrated solution diffuses through a semipermeable membrane to a more concentrated solution. The semipermeable membrane is selective, i.e., allowing water molecules to pass while retaining total dissolved solids ("TDS").

Reverse osmosis is a phenomenon that is achieved when pressure is supplied to a concentrated solution in order to drive water through a semi-permeable membrane and away from the concentrated solution, against osmotic pressure. The dissolved and particulate matter in the concentrated solution remain behind. The proportion of salts to water in the concentrated solution will therefore increase, with a corresponding increase in the osmotic pressure. Thus, the higher the percentage of pure water that is extracted from the salt solution, the greater the pressure that must be exerted on that solution.

Reverse osmosis ("RO") has evolved into a common, reliable, and economical method to purify water. This treatment method purifies water by continuously concentrating and removing contaminants from a feed stream with relatively low energy and chemical usage.

In operation, it is important that the RO system be sampled periodically in order to generate a conductivity profile along the length of the pressure vessel. This sampling is performed in order to assure the quality of the process. Typical determinations include conductivity in-line readings in both the feed and permeate streams, which are expressed in terms of "micro MHO's". This data can then be used to calculate the percent salt rejection. A loss in percent salt rejection may or may not be accompanied by changes in other RO performance indicators.

For instance, it is recommended that as a routine monitoring procedure, it is useful to obtain a periodic conductivity profile of each pressure vessel within an RO system. Such monitoring can be used to identify and assess a number of parameters, including fouling of the vessel, operating conditions, mechanical failure, and anticipated clean-up procedures.

The technique most commonly used to sample the permeate, particularly when using spiral wound membrane systems, presently involves having technicians manually probe the vessel with tubing. Commonly a ¼ inch polypropylene tube is used, which is provided in a sufficient length to traverse the length of the vessel through the permeate line. (See, e.g., Bukay, et at., *Ultrapure Water*, pp. 62, March/April 1986). Analysis of samples drawn from the tube at various positions within the RO system allows the technicians to identify membrane system irregularities.

In what appears to be the most common practice presently used, the tube is inserted by hand into the full length of the permeate tube. The TDS of the permeate sample from the tubing is measured with a hand-held TDS meter. The tube is withdrawn and the procedure is repeated until a TDS profile of each element is obtained.

Probing is typically accomplished by removing the vessel's product manifolds, on one end of the vessel, or by removing the permeate plug on the opposite end of the vessel. While the RO system is operating at normal pressure water then flows from the permeate tube of the vessel, i.e., in the reverse direction of the normal flow. A tube is inserted and made to traverse the length of the pressure vessel. After a few minutes, to allow the RO system to equilibrate, the TDS of the permeate is measured in an incremental fashion along the length of the vessel.

One significant drawback commonly associated with such probing methods is the fact that there is frequently significant permeate loss and spillage associated with the removal of the permeate plug. Similarly, such sampling processes are particularly inconvenient since they often require two technicians. Technicians typically need to remove the permeate plug from the vessel and keep the permeate plug off for the duration of the sampling process.

The water that is spilled in the course of the sampling process not only adds to the inconvenience, but also affects the operation of the pressure vessel itself. The loss of water leads to a change in the direction of water flow within the vessel, as permeate flows from other units (in a multi-pressure vessel system) or from other portions of the same unit. The present sample process can also lead to inaccuracies, as the result of permeate contaminating the sample region.

It would clearly be desirable to have an apparatus and method for sampling the liquid contents of vessels, and in particular for probing the permeate stream of a pressure vessel, in a manner that avoids these drawbacks, yet that is efficient, effective, and inexpensive.

DISCLOSURE OF THE INVENTION

The present invention provides a sample valve for use in a port of a liquid-containing vessel. The valve incorporates a housing that can be sealably attached to the vessel port. The apparatus, in turn, can be operated to allow access of a sampling tube or other implement through the apparatus, and in turn through the vessel port and into the vessel, with minimal or no loss of fluids or pressure.

In a preferred embodiment, the valve provides the unique ability to insert and retain a sampling tube into the valve at a first position that is less than fully inserted within the sample valve. The tube can then be retained in its first position without substantial loss of vessel contents. With the tube in its inserted, retained position the valve can then be completely opened in order to allow the tube to be fully inserted into the vessel, also without the substantial loss of liquid or pressure from the vessel.

In a particularly preferred embodiment, the present invention provides a pressure vessel sample port valve that overcomes the problems associated with the need to remove a permeate plug in order to probe and sample a reverse osmosis permeate line. The valve of the present invention is particularly useful since it not only allows sampling of a permeate line, but it can also be used as a permanent replacement for the conventional plug. The valve therefore does not need to be removed, except infrequently for purposes of shutdown and other routine maintenance.

The valve of the present invention allows a technician to feed a sampling tube into a pressure vessel, with the valve in place, in order to sample the permeate stream under normal operating conditions. Since the valve can be used in place of a traditional permeate plug, it avoids the need to remove a permeate plug in order to feed a sampling tube.

In such a preferred embodiment, according to the present invention there is provided a sample port valve for use in a port of a liquid-containing vessel, the valve comprising:

a housing comprising a port attachment end and an opposite sampling end, the housing having an overall length dimension extending between the ends, the housing further comprising;
  (a) an attachment mechanism associated with the attachment end of the housing for sealingly connecting the housing to the vessel port;
  (b) a passageway disposed within and traversing the overall length of the housing and dimensioned to allow a sampling tube to traverse the overall length of the housing; and
  (c) an access control assembly operably associated with the passageway in order to open and close the full length of the passageway to the passage of the tubing, whereby
    (i) with the access control assembly in a closed position, the tubing can be inserted into the sampling end of the housing and can traverse and be sealingly retained in the passageway to a first position less than the full length of the passageway, and
    (ii) with the tubing at its first, retained position, the access control assembly can be operated in order to open the full length of the passageway, and
    (iii) with the access control assembly in the open position, the retained tubing can be further inserted in order to traverse the full length of the passageway.

BRIEF DESCRIPTION OF THE DRAWING

The present invention will be further described with reference to the accompanying Drawing wherein like reference numerals refer to like parts in the several views, and wherein.

DETAILED DESCRIPTION

Figure 1:
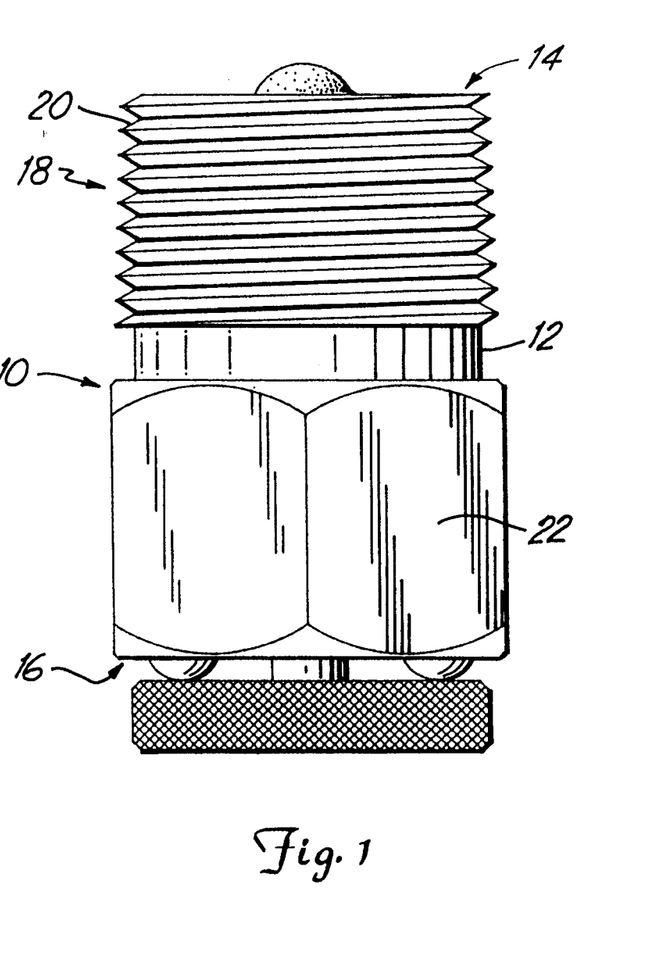
FIG. 1 is a front view of a preferred embodiment of a valve of the present invention.
Figure 2:
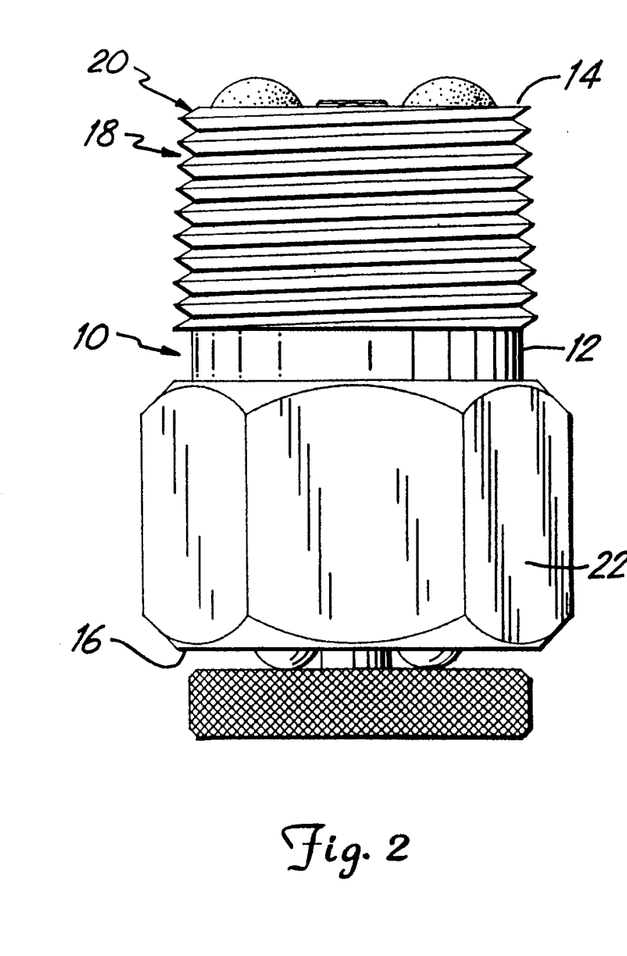
FIG. 2 is a right side view of the valve shown in FIG. 1.

Referring now to FIG. 1 of the Drawing, there is shown a preferred embodiment of a valve according to the present invention, generally designated by the reference number 10. FIG. 2 shows a similar view of the same valve, although rotated 90 degrees to show additional detail. Valve 10 comprises a generally cylindrical housing 12 having a port attachment end 14 and an opposite tubing access end 16. Housing 12 comprises attachment mechanism 18 associated with the housing, useful for sealingly engaging the housing in the permeate port of a pressure vessel (not shown).

In a preferred embodiment, attachment mechanism 18 comprises a male region having an outside thread 20 forming the exterior circumference of port attachment end 14. A preferred attachment mechanism further comprises hexagonal wrench flats 22 associated with and forming the exterior circumference of the tubing access end 16. With the valve in position within a suitably sized female threaded port, the wrench flats can be grasped within the jaws of a wrench and rotated in order to sealingly engage the housing into the port. Clearly any suitable means can be used to achieve the sealed attachment of a valve of the present invention on or into a permeate port.

As used in the context of the present invention, the word "sealed", and inflections thereof, shall refer to the ability of a valve of the present invention, and its component parts, to be used in the port of a vessel in a manner that prevents the leakage or spillage of the contents of the vessel to the desired extent.

Figure 3:
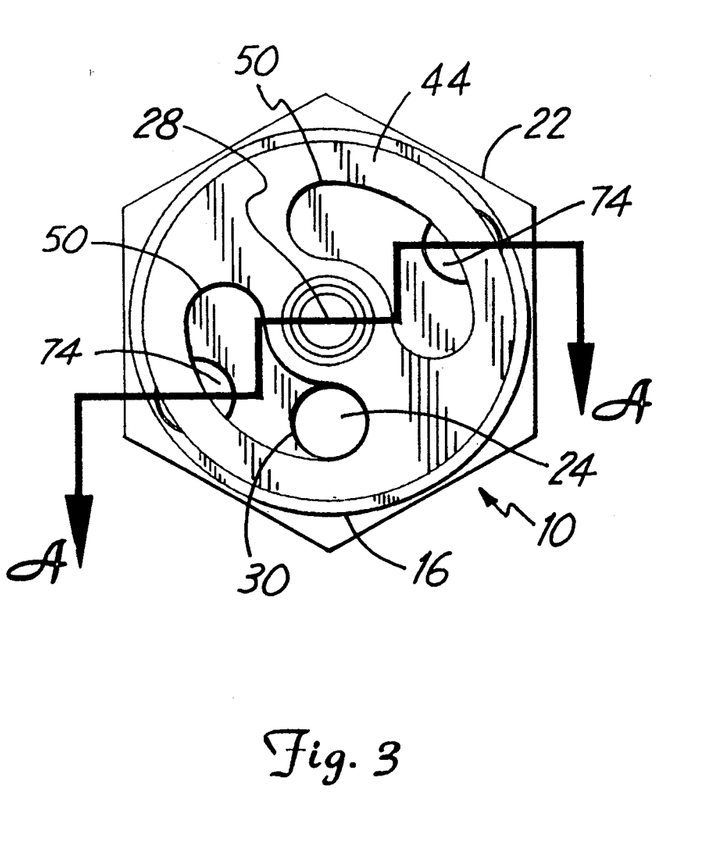
FIG. 3 is a bottom view of the valve shown in FIG. 1.
Figure 4:
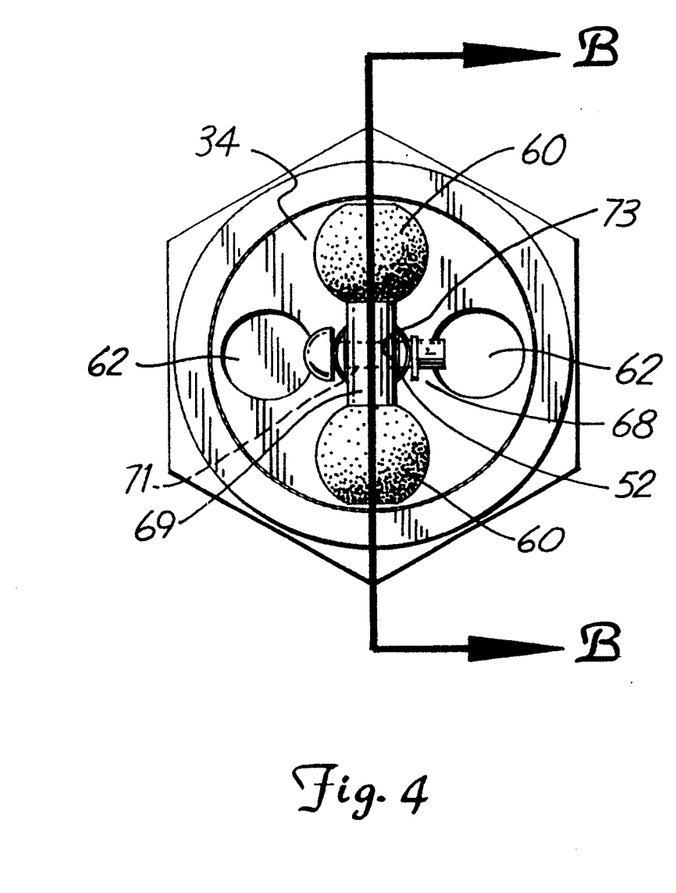
FIG. 4 is a top view of the valve shown in FIG. 1.

FIGS. 3 and 4, which will be described in greater detail below, show detail of both the right and left ends of a valve of the present invention. FIG. 3 shows a view through the knurled handle and into the passageway, while FIG. 4 shows a view from the opposite end, including sealing balls in position to block the exit from the passageway.

Figure 5:
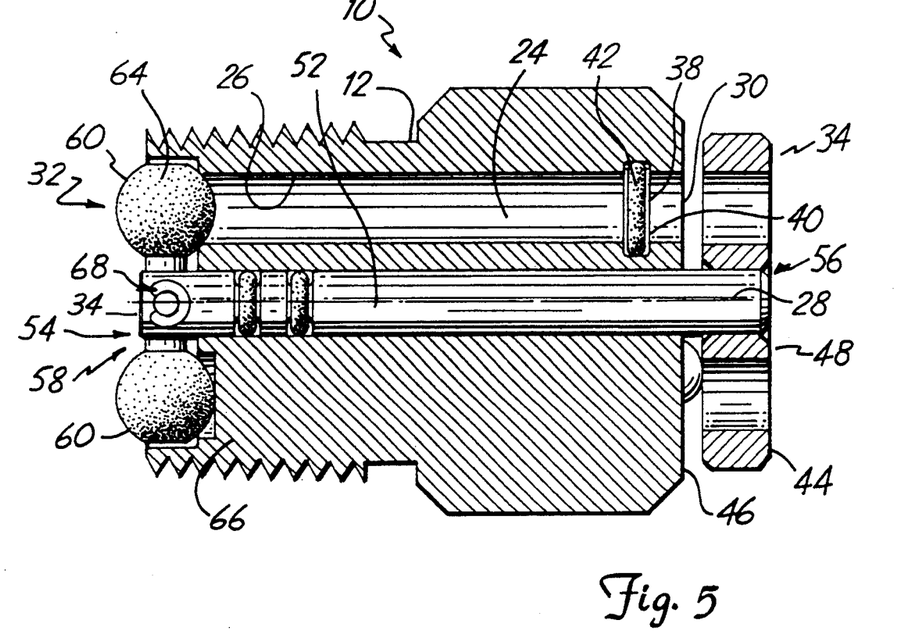
FIG. 5 is a cross-sectional view taken along lines B—B of FIG. 4.
Figure 6:
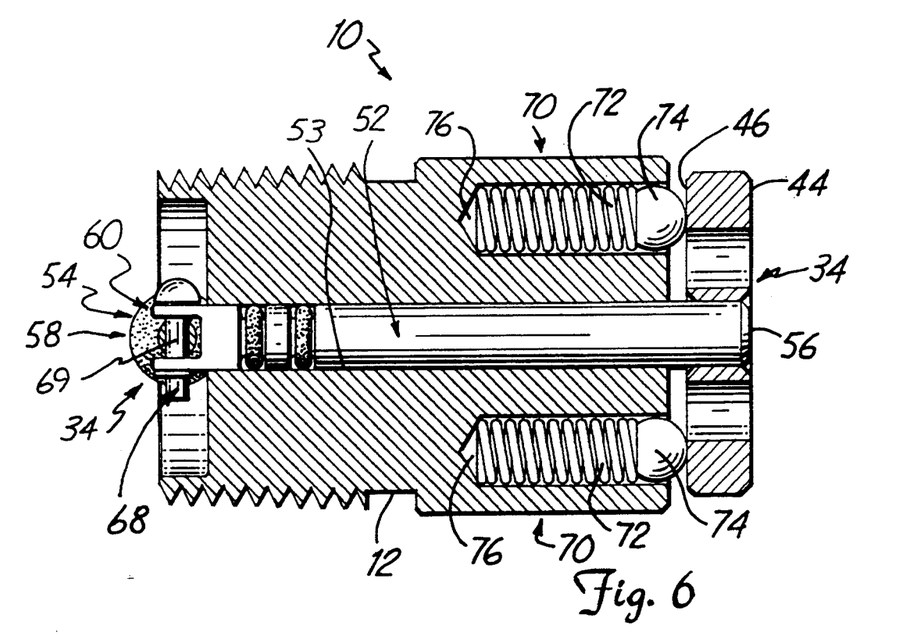
FIG. 6 is a cross-sectional view taken along lines A—A of FIG. 3.

Turning next to FIG. 5 and 6 there are seen cross-sectional views of FIGS. 4 and 3, respectively. It can be seen that housing 12 further comprises a tubing passageway 24 in the shape of a continuous tubular passage comprising a substantially cylindrical inner surface 26 traversing and substantially in axial alignment with the housing. As shown, passageway 24 is preferably in a position that is nonconcentric with center axis 28 of housing 12. Passageway 24 provides inlet and exit ends, 30 and 32 respectively. Passageway 24 is dimensioned to allow a sampling tube (not shown) to be inserted in the inlet end and to traverse the length of the passageway, extending through and beyond the exit end and into a pressure vessel.

Passageway 24 further comprises an access control assembly 34 for controlling the access of a tube through the full length of the passageway. Access control assembly 34 preferably controls the access of the tube in two respects. First, it allows a tube to be inserted into passageway 24 in such a manner that it will be sealingly retained at a position short of fully traversing passageway 24 within housing 12.

Access control assembly 34 can then be operated by a technician, with an inserted tube retained in a first position, in order to allow the retained, partially inserted tube to be fully inserted into and to a second position through housing 12. In this respect, a preferred access control assembly includes operably connected, moveable access blocking balls 60. When turned into position overlaying the exit end 32 of the passageway 24, the blocking balls 60 are used to prevent a tube from fully traversing the length of the passageway into the pressure vessel. In order to retain an inserted tube in a sealed relationship short of fully traversing the housing, passageway 24 further preferably comprises a retaining assembly 38. As shown, retaining assembly 38 comprises a recessed groove 40 within the surface 26 of passageway 24, and concentric with the passageway. The groove is positioned at a desired distance along the length inner surface of the passageway. Retaining assembly 38 also comprises an O-ring 42, which is dimensioned to be replaceably retained at its outer circumference within groove 40. O-ring 42 is also dimensioned to provide a sealed engagement between its inner circumference and an inserted sampling tube.

Access control assembly 34 comprises a grasping disc 44 having a circumference that is preferably substantially the same as the circumference of housing 12. Disc 44 is shown having substantially fiat interior and exterior major surfaces 46 and 48, respectively. Disc 44 is preferably dimensioned to allow it to be grasped by a technician such that it can be rotated upon its central axis in order to open and close access to the full length of passageway 24, by moving either blocking ball into or out of a position blocking the exit end of the passageway. In this respect, the outer circumference of disc 44 can be knurled or otherwise provided with a textured surface that facilitates the grasping and turning of the disc.

Reference shall now be made to FIG. 3, in which it can be seen that in a preferred embodiment, disc 44 further comprises a plurality of opposing kidney shaped apertures 50 traversing the thickness of disc 44 and following a path that is generally concentric with the outer circumference of the disc. With the valve in a closed position, the apertures are positioned in such a manner that at least one of them will overlay the inlet end of passageway 24, such that a sampling tube can be inserted through the overlaying aperture and into the inlet.

In use, and with the valve in its closed position, tubing is placed through whichever aperture happens to overlay passageway 24, and inserted into housing 12 until a point beyond the retaining O-ring. The tubing is pushed into the housing such that the end of the tube will extend beyond the O-ring within the passageway, in order to achieve a seal, and either short of, or blocked, by the moveable sealing ball covering and making sealing contact with the exit end of passageway 24.

After the tube has been inserted and retained in its inserted position, the valve can be opened by rotating the disc approximately 90 degrees. As discussed further below, rotation of the disc opens the full length of the passageway, by removing the blocking ball, and allows the tube to be fully inserted to the desired position within the permeate line.

Apertures 50 are therefore each preferably provided having a width dimension sufficient to allow the insertion of a tube having a desired predetermined diameter, and having an arcuate length dimension at least twice the predetermined diameter of the tube. In this manner the disc can be rotated, with the tube retained in the housing, in order to open or close access to the full length of the passageway.

Turning back to FIGS. 5 and 6, disc 44 is shown as being operably attached, at approximately the center point of its interior surface 46, to central shaft 52. Shaft 52 is itself retained in axial alignment with the center of the housing within and by means of a shaft cavity 53. Shaft 52 comprises interior and exterior ends, 54 and 56 respectively. By virtue of its operable attachment to the interior surface 46 of disc 44, shaft 52 can rotated upon rotation of the disc.

In order to prevent an inserted tube from fully traversing passageway 24, access control assembly 34 also comprise ball sealing assembly 58 operably attached to interior end 54 of shaft 52. Ball sealing assembly 58, in turn, preferably comprise a plurality of moveable sealing balls 60, a plurality of ball detent seats 62 on the base of the housing (not shown in FIG. 2), a passageway seat 64 covering the exit end of passageway 24, and a passageway detent seat 66, for receiving one sealing ball while the opposite sealing ball covers the exit end of passageway 24. The edges of both the detent seats and the exit end of passageway 24 are preferably tapered or beveled slightly in order to facilitate the movement of the blocking balls into and out of position therein.

Figure 7:
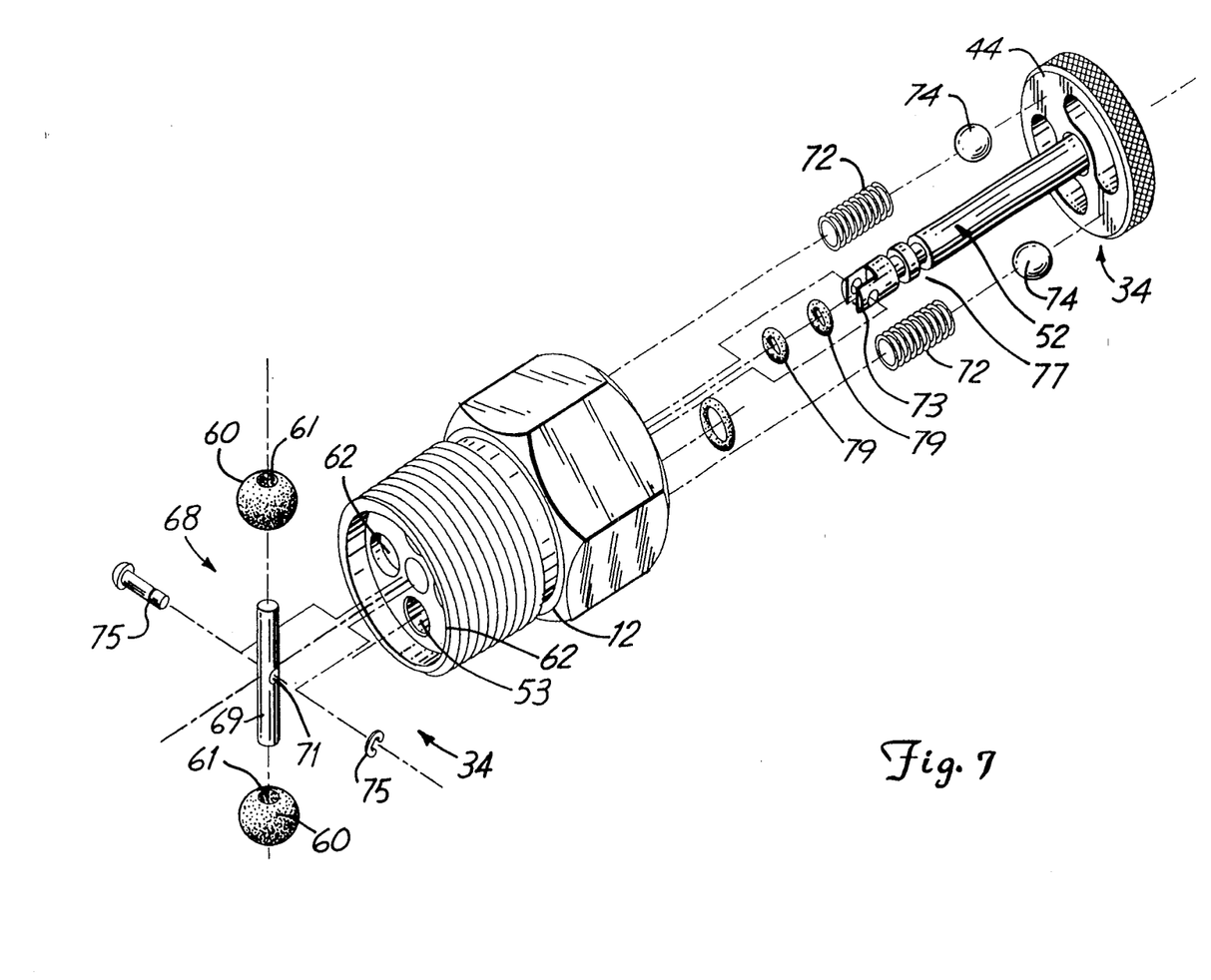
FIG. 7 is an exploded isometric view of the valve shown in FIG. 1.

Turning briefly to FIGS. 4 and 7, it can be seen that the ball sealing assembly of access control assembly 34 further comprises ball retaining assembly 68 for holding balls in operable relationship with shaft 52. In a preferred embodiment, moveable sealing balls 60 are each provided with a central aperture 61. Correspondingly, retaining assembly 68 is provided in the form of a rod-like member 69 for the retained placement of sealing balls. The rod-like member 69 itself is formed with an aperture 71 at the midpoint of its length, with is used to releasable engage the rod-like member within a notched aperture 73 in the end of the shaft by means of a pin and collar assembly 75 retained by an annular groove snap joint.

The opposite ends of rod-like member 69 are each dimensioned to be retainably inserted, as by a slip fit, into the central apertures 61 of the sealing bails 60. Rod-like member 69 is itself retained in position within aperture 73 of the notched end 54 of central shaft 52. Preferably, the rod is inserted through an aperture through the end of the central shaft, which aperture is dimensioned to hold the rod-like member at approximately its center point. The rod-like member retained in the shaft by means of a pin through a hole in the shaft, the pin allowing the rod to pivot about an axis perpendicular to the axis and the shaft. Shaft 52, in turn, preferably includes grooves 77 and corresponding shaft O-rings 79, which are used to provide a seal to the passage of fluids or pressure loss through the shaft cavity.

Turning briefly back FIG. 6, the access control assembly associated with housing 12 further comprises biasing assembly 70 for biasing the disc 44 away from housing 12 when balls are retained in opened and closed positions. In this preferred embodiment, biasing assembly 70 comprises a plurality of coil springs 72 and a plurality of biasing bails 74 housed within recessed compartments 76 within housing 12. Springs 72 are disposed within recessed compartments 76 such that they abut against the inner surface of the solid housing, on one end, and against the biasing balls 74 on their opposite ends.

The biasing bails, in turn, abut the inner major surface 46 of disc 44 at substantially a point on each biasing ball that on the central axis of, and opposite, the respective biasing spring. The springs are provided having a stiffness sufficient to allow the disc to be manually rotated. The stiffness of the coil springs is sufficient to cause the disc to be appropriately maintained at a distance away from the body of the housing according to the position of sealing balls. When the valve is in its fully opened or closed positions, i.e., both sealing balls are seated within either detent positions and/or in a position covering the exit end of passageway 24, the disc will accommodate the depth to which the bail sits within the passageway by resting at its furthest distance from the housing.

Similarly, when the valve is in a position intermediate between opened and closed, i.e., when the sealing balls are on a surface of the housing that is between and above the detent seats, the biasing assembly will ensure that the disc is retained at its closest position to the housing.

In use, with the access control assembly in the closed position, a tube can be inserted through the grasping disc into the entry inlet of the passageway and beyond the O-ring up to the region of the sealing ball blocking the interior end of the passageway. Once inserted, the tube is retained in position, by virtue of its fit within the passageway and particularly the O-ring inside the passageway, in order to sealingly engage the tube in the passageway. The tube can be left in the inserted, retained position, although it is preferable to immediately proceed to the step of fully inserting the tube into the vessel by opening the valve.

After inserting the tube, therefore, with the tube still retained in its inserted position, the disc can be grasped and rotated 90 degrees in order to open access control assembly. Such assembly functions to open the passageway by turning the sealing ball out of its position in the passageway blocking seat and into an adjacent detent position. The tubing can then be fully inserted through the valve and into the vessel. Using tubing that is calibrated or otherwise marked along its length, the tubing can be inserted such that its open end is positioned at, and samples drawn from, any desired point within the vessel. When the sampling process is completed, the tubing can be retracted and removed from the vessel and valve by reversing the order of steps used to insert it. By the use of simple measurement or markings the tube can be withdrawn to a point where its end is known to be within the exit end of the valve passageway, yet beyond the position of the sealing. O-ring. The valve can then be closed, in order to close the exit end of the passageway to the flow of fluid, and the tubing fully withdrawn.

The valve of the present invention is intended to be used with any suitable liquid containing vessel, e.g., in which it is desired to sample the contents of the vessel at various times and points, and in a manner that causes minimal perturbation of the vessel contents. The valve is suitable, for instance, for sampling the contents of wine casks, distribution lines, storage tanks, or decanter vessels.

Figure 8:
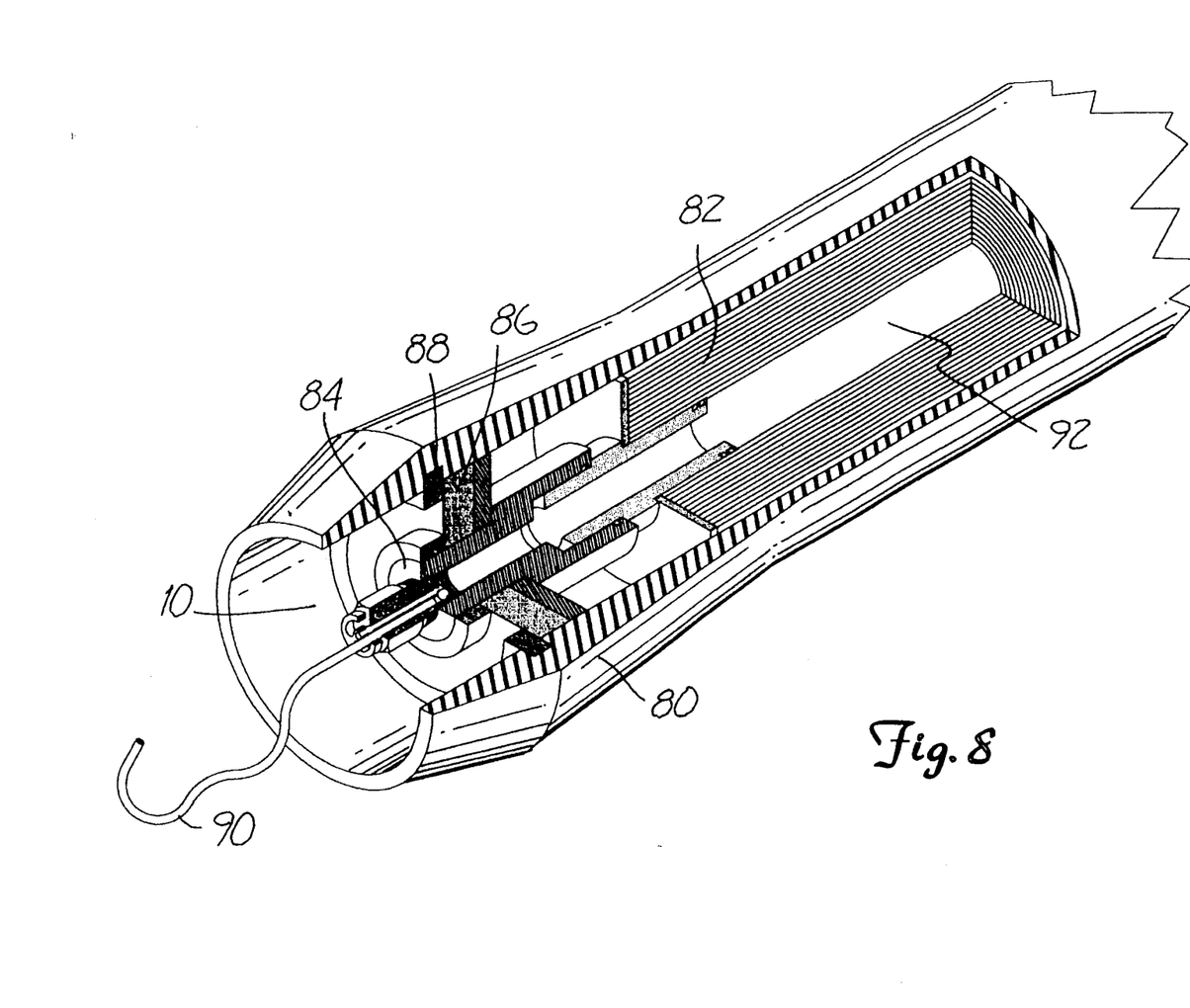
FIG. 8 is an isometric view of a reverse osmosis pressure vessel having a valve of the present invention in place and in the closed position, with sample tubing inserted to a first, retained position.
Figure 9:
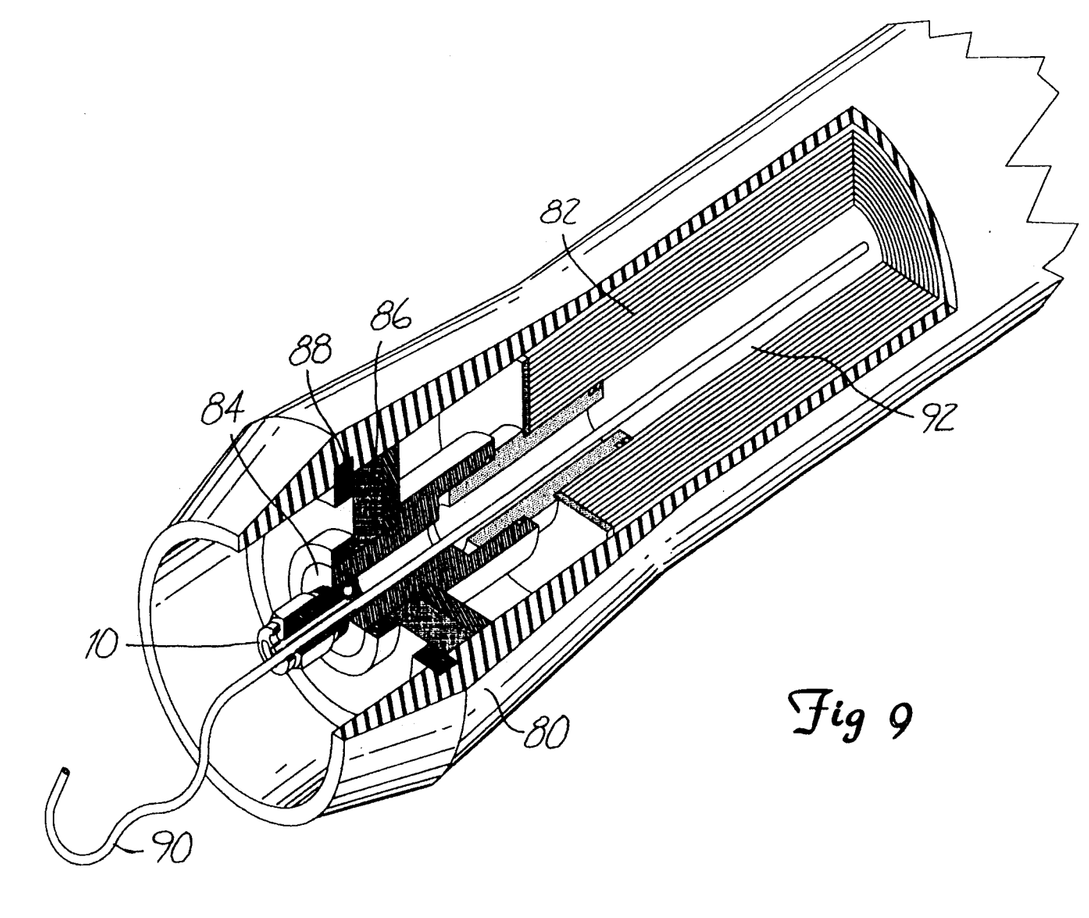
FIG. 9 is an isometric view of the vessel of FIG. 9 with the valve in the fully open position and the sampling tube inserted and traversing the passageway into the pressure vessel.

In a preferred embodiment, the valve is useful for sampling procedures associated with reverse osmosis systems, and preferably with RO systems that involve the use of spiral wound membranes. Typically, an RO system will involve a pressure vessel containing spiral wound membranes. Relevant portions of a common vessel are depicted in FIGS. 8 and 9 where it can be seen that the vessel 80 comprised of a shell forming a generally cylindrical tube, having a desired length. The shell can be made of any suitable material, such as a filament wound epoxy glass composite material. On each open end of the cylindrical shell there are typically headlocking grooves integrally wound in place.

As seen in FIGS. 8 and 9, membrane element 82 is retained within the vessel 80. There can be seen an apparatus 10 of the present invention retained in position in end cap orifice 84 of the end cap 86, held in place by locking ring 88 of the pressure vessel assembly. Also shown is ¼" sampling tube 90 inserted into valve 10. In FIG. 9 the sampling tube is shown fully inserted through valve 10 and into the permeate tube 92 traversing the center of membrane element 82.

The conventional shell is connected to a pressure vessel head unit, which involves a bearing plate and a sealing plate, the plates comprising both a feed/concentrate port and a permeate port, both with related seals. The head is retained in sealed engagement with the vessel shell by means of head interlock mechanism, generally including a locking ring set and securing rings and screws. The vessel also provides a support mechanism, such as a saddle and strap mechanism (not shown). Prior to the valve of the present invention, the permeate port has typically been covered with a port plug, generally of a PVC thermoplastic material having a right handed thread.

Within the shell are contained the RO membranes, the detail of which will not be shown, other than to point out that they comprise a central permeate line. The vessel shell itself will typically provide an interface element comprising a thermoplastic adaptor, together with thrust and adaptor rings and seals in order to provide a sealed engagement between the vessel shell and the membranes.

Reverse osmosis membranes are typically available in three forms: single sheets, hollow fibers, and spiral wound sheets. The sampling caps of the present invention are particularly useful with spiral wound membrane systems, which are generally the choice for commercial use. Spiral wound elements offer a large membrane surface area within a compact unit and are resistant to high transmembrane differential pressure.

A sample port valve of the present invention is used as a replacement for the use of a conventional port plug opposite the permeate collection piping on an RO vessel. The valve is preferably disposed in and attached to the permeate port of the vessel in the same manner as a port plug, and in sealed engagement therewith.

Valves of the present invention can be used to sample the liquid from within a liquid-containing vessel. A first step of such a method generally includes the step of inserting or otherwise attaching the valve to the exit port of the vessel in order to form a sealed relationship.

In use, the technician inserts the sampling tube into the passageway of the valve. The sampling tube is inserted to a point beyond the O-ring contained in the passageway, such that the tube is or can be retained in such position as the valve is fully opened. Once the tube is in its inserted position, the technician can open the full path length of the passageway of a preferred valve by simply turning the disc that operates the controller. When the passageway has been opened, the technician continues to insert the tube to its desired position or length within the vessel.

A technician can determine the appropriate sampling procedure based on techniques that will be well within the skill of those in the art. A technician can, for instance, use a tube that is itself graduated in increments that tell the technician the distance that the tube has entered the vessel. When the tube has reached its desired position(s) the technician can proceed to retain samples of the liquid from such position.

When the sampling procedure has been completed, the technician can remove the tubing and close the passageway by essentially reversing the order of steps involved in beginning the sampling procedure.

Valves of the present invention can be manufactured using materials and forming methods well within the skill of those in the relevant art. Valves, including any component parts of such valves, can be prepared using any materials capable of providing the desired combination of machinability, strength, inertness, impact toughness, cost, and resistance to impact, abrasion, radiation cyclical fatigue, environmental stress-crack. Examples of suitable materials include metals such as stainless steel, and high density plastics, such as high density polyethylene and ultrahigh molecular weight polyethylene. For the manufacture of sampling valve for permeate ports of RO systems, an example of a preferred material is stainless steel.

Typically the housing will be formed from as a single piece, e.g., formed from hexagonal stock. The component parts of the access control assembly will then be separately formed, and the valve itself constructed from its respective parts.

The balls of such a preferred valve are preferably formed from a more resilient material, such as rubber, in order to improve their wear characteristics and optimize their ability to be moved between positions and to become sealingly engaged in a ball seat.

A sample port valve of the present invention was prepared in the manner described herein and evaluated. The valve was machined using 316 stainless steel, beginning with 1⅜ hex stock, and was passivated after machining. The final valve had an overall length of approximately 2½ inches, and an overall width, across its wrench flats, of 1⅜".

The sample port valve was tested on a 225 gallon per minute reverse osmosis unit. The permeate plug of the end cap pressure vessel was removed and replaced with the sample port valve. The permeate pressure was approximately 20 psi and during normal operation of the reverse osmosis unit there was no apparent leakage.

The valve was then used to perform conductivity profile sampling and performed well. The valve easily allowed one technician to perform the entire sampling function. The sampling was performed with no uncontrolled permeate spillage. Tubing slid through the valve smoothly and traversed the permeate tube of the reverse osmosis element with no difficulty.

The valve was able to withstand a pressure of over 100 pounds per square inch (psi) of water pressure in a test apparatus for a 24 hour period with no loss of pressure or liquid. This performance is well in excess of the specifications that would need to be met in order to use the valve in a practical application.

The pressures typically encountered in routine applications are generally on the order of less than 50 psi. It would appear, therefore, that the valve of the present invention is suitable for use in the demanding application of RO systems.

The present invention has now been described with reference to various embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

What is claimed is:

1. A sample port valve for use in a port of a liquid-containing vessel, said valve comprising:
    a housing comprising a port attachment end and an opposite sampling end, said housing having an overall length dimension extending between said ends, said housing further comprising;
    (a) an attachment end associated with said housing for sealingly connecting said housing to said vessel port;
    (b) a passageway disposed within and traversing said overall length of said housing, said passageway being dimensioned to allow a sampling tube to traverse said overall length of said passageway; and
    (c) an access control assembly operably associated with said passageway in order to open and close said full length of said passageway to the passage of said tubing, whereby
        (i) with said access control assembly in a closed position, said tubing can be inserted into said sampling end of said housing and can traverse and be sealingly retained in said passageway to a first position less than said full length of said passageway,
        (ii) with said tubing in said retained position, said access control assembly can be operated in order to open said full length of said passageway, and
        (iii) with said access control assembly in said open position, said retained tubing can be further inserted in order to traverse said full length of said passageway.

2. A sample port valve according to claim 1 wherein said housing is substantially cylindrical in shape having an exterior circumference, and said attachment end comprises a threaded male region forming said exterior circumference of said port attachment end, and wrench flats associated with said exterior circumference of said tubing input end, whereby said wrench flats are capable of being grasped and rotated in order to sealingly engage said housing into a female threaded permeate port.

3. A sample port valve according to claim 2 wherein said passageway comprises a substantially cylindrical inner surface traversing and in axial alignment with the axis of said substantially cylindrical housing, said passageway being in a position nonconcentric with said center axis of said housing, having inlet and exit ends, and being dimensioned to allow a sampling tube to be inserted in said inlet end and to traverse said length of said passageway through said exit end.

4. A sample port valve according to claim 3 wherein said passageway has a recessed groove concentric with said substantially cylindrical housing and within and along the length of said inner surface of said passageway, and said valve further comprises an O-ring dimensioned to be replaceably retained within said passageway groove and to provide a sealed engagement with an inserted sampling tube.

5. A sample port valve according to claim 1 wherein said housing further comprises a cylindrical compartment traversing said center of said housing, and wherein said access control assembly comprises;

(a) a central shaft retained in axial alignment within said compartment, said shaft having interior and exterior ends and being operably attached at its exterior end to said interior surface of said grasping disc in a manner that allows said shaft to be rotate upon rotation of said handle;

(b) a ball sealing assembly operably attached to said interior end of said shaft, said ball sealing assembly comprising a plurality of sealing balls, a plurality of ball detent seats for retaining said sealing balls with said passageway in said open position, a passageway seat for retaining a first sealing ball in position to close said passageway, and a passageway detent seat for retaining a second sealing ball with a first sealing ball in position to close said passageway; and (c) a grasping disc having a circumference substantially said same as said circumference of said housing and having substantially flat interior and exterior major surfaces, said disc being dimensioned to allow it to be grasped and rotated upon a central axis in order to open and close access to a tube through said passageway.

6. A sample port valve according to claim 5 wherein said disc comprises a plurality of opposing kidney shaped apertures traversing said disc and concentric with said circumference of said disc, said apertures each having a width dimension sufficient to allow insertion of a tube having a predetermined diameter, and an arcuate length dimension at least twice said predetermined diameter of said tube.

7. A sample port valve according to claim 5 wherein said ball sealing assembly further comprises a ball retaining assembly for holding balls in an operable relationship with said shaft, said retaining assembly being provided in the form of a rod-like member for said retaining said sealing balls; said rod-like member retained in said shaft by means of a pin through an aperture in the shaft, thereby allowing the rod to pivot about an axis perpendicular to the axis and the shaft.

8. A sample port valve according to claim 5 wherein said access control assembly further comprises a biasing assembly for biasing said grasping disc against said housing, said biasing assembly comprising a plurality of springs axially aligned with said axis of said housing and operably positioned against a plurality of biasing balls within recessed compartments within said housing.

9. A sample port valve according to claim 1 wherein said vessel is a pressure vessel comprising a permeate port, and said valve is dimensioned to be sealingly engaged in said permeate port.

10. A combination comprising a pressure vessel having a permeate port and a sample port valve according to claim 1, wherein said valve is disposed in a sealed engagement with said permeate port of said pressure vessel.

11. A method of sampling liquid from within a liquid-containing vessel having a sample port, the method comprising the steps of providing a valve according to claim 1, sealingly engaging said valve into said port, inserting sampling tubing to a first position within said valve, operating said access control assembly in order to open said passageway through said valve, inserting said tubing through said passageway, and sampling liquid at desired positions within said vessel.

* * * * *